US009289124B2

(12) United States Patent
Bonaventura et al.

(10) Patent No.: US 9,289,124 B2
(45) Date of Patent: *Mar. 22, 2016

(54) TONOMETER CALIBRATION TOOL

(71) Applicant: Reichert, Inc., Depew, NY (US)

(72) Inventors: Russell Bonaventura, Williamsville, NY (US); David G. Kelkenberg, Akron, NY (US); David L. Beverly, Alden, NY (US); Donald E. Miller, La Quinta, CA (US); David A. Luce, Clarence Center, NY (US)

(73) Assignee: REICHERT, INC., Depew, NY (US)

(*) Notice: Subject to any disclaimer, the term of this patent is extended or adjusted under 35 U.S.C. 154(b) by 16 days.

This patent is subject to a terminal disclaimer.

(21) Appl. No.: 14/326,023

(22) Filed: Jul. 8, 2014

(65) Prior Publication Data

US 2014/0323843 A1    Oct. 30, 2014

Related U.S. Application Data

(62) Division of application No. 13/278,214, filed on Oct. 21, 2011, now Pat. No. 8,800,347.

(51) Int. Cl.
*A61B 3/16* (2006.01)
*G01L 27/00* (2006.01)

(52) U.S. Cl.
CPC .............. *A61B 3/165* (2013.01); *G01L 27/002* (2013.01)

(58) Field of Classification Search
USPC ........................................................ 73/1.57
See application file for complete search history.

(56) References Cited

U.S. PATENT DOCUMENTS

| 3,282,090 | A | * | 11/1966 | Posner | A61B 3/16 600/405 |
| 3,287,957 | A | * | 11/1966 | Martens | A61B 3/16 600/405 |
| 3,736,789 | A | * | 6/1973 | Drew | G01L 27/005 73/1.57 |
| 3,889,518 | A | * | 6/1975 | Denouter | G01L 27/00 73/1.66 |
| 4,220,038 | A | * | 9/1980 | Kantorski | A61B 3/16 73/1.08 |
| 4,834,105 | A | * | 5/1989 | Matthews | A61B 3/165 600/401 |
| 5,474,066 | A | * | 12/1995 | Grolman | A61B 3/165 600/398 |
| 5,644,375 | A | * | 7/1997 | Suzuki | A61B 3/165 351/208 |

(Continued)

FOREIGN PATENT DOCUMENTS

JP    11-225974 A    8/1999

*Primary Examiner* — Peter Macchiarolo
*Assistant Examiner* — Alexander Mercado
(74) *Attorney, Agent, or Firm* — Hodgson Russ LLP

(57) ABSTRACT

A tool for calibrating a non-contact tonometer (NCT) comprises a body having a mating feature configured for removably mounting the body on the nosepiece or on the measurement head of the NCT, a pressure sensor carried by the body and arranged to receive an air pulse discharged by the NCT to provide a pressure signal in response to the air pulse, and a radiation emitter carried by the body, wherein the radiation emitter provides a pseudo-applanation event when the pressure signal reaches a predetermined level that is detectable by the NCT as though an actual corneal applanation had taken place. In one embodiment, the mating feature includes a mounting orifice for receiving a portion of the nosepiece. In another embodiment, the mating feature includes a pair of mounting pins sized for receipt by a corresponding pair of mounting holes in the measurement head of the NCT.

4 Claims, 8 Drawing Sheets

(56) References Cited

U.S. PATENT DOCUMENTS

| | | | |
|---|---|---|---|
| 5,868,580 A * | 2/1999 | Amrein | G09B 23/28 434/271 |
| 6,419,631 B1 * | 7/2002 | Luce | A61B 3/165 600/401 |
| 6,679,842 B2 | 1/2004 | Luce | |
| 7,556,380 B2 | 7/2009 | Cohan et al. | |
| 7,909,462 B2 * | 3/2011 | Takahashi | A61B 3/0083 351/208 |
| 8,800,347 B2 * | 8/2014 | Bonaventura | A61B 3/165 73/1.57 |
| 2003/0195430 A1 * | 10/2003 | Luce | A61B 3/165 600/559 |
| 2004/0002639 A1 * | 1/2004 | Luce | A61B 3/165 600/398 |
| 2004/0002640 A1 * | 1/2004 | Luce | A61B 3/165 600/399 |
| 2007/0055122 A1 * | 3/2007 | Luce | A61B 3/165 600/405 |
| 2008/0021298 A1 * | 1/2008 | Cohan | A61B 3/16 600/399 |
| 2012/0162605 A1 * | 6/2012 | Koest | A61B 3/165 351/221 |

* cited by examiner

TONOMETER CALIBRATION TOOL

FIELD OF THE INVENTION

The present invention relates generally to non-contact tonometers that measure intraocular pressure (IOP) by directing a fluid pulse at the cornea, and more particularly to a tool for calibrating such non-contact tonometers.

BACKGROUND OF THE INVENTION

Existing non-contact tonometers measure IOP by activating a pump mechanism to fire an air pulse at the cornea to flatten or "applanate" a predetermined area of the cornea, detecting corneal applanation caused by the air pulse and a plenum pressure of the pump mechanism, and correlating the plenum pressure at the moment of applanation with IOP. In older instruments, the time elapsed to achieve applanation was correlated to IOP as an indirect representation of plenum pressure based on a linearly increasing pressure profile in the plenum. In present day instruments, a pressure sensor is mounted in the plenum for providing a signal proportional to the plenum pressure. Regardless of whether elapsed time or a signal from a pressure sensor is obtained, it is necessary to correlate the obtained quantity to IOP such that the instrument provides a meaningful measurement value of IOP as output. Thus, non-contact tonometers must be calibrated periodically to ensure that the correlation function used by the particular instrument yields IOP results that are substantially in agreement with an established standard of IOP measurement.

Traditionally, the Goldmann applanation tonometer (GAT), which measures IOP by directly contacting the cornea to applanate an area of the cornea, has been used as a standard for IOP measurement. Accordingly, initial calibration of a non-contact tonometer has been carried out by way of a clinical trial involving a large number of human eyes. During the clinical trial, each eye is measured with both GAT and the subject non-contact tonometer, and the parameters of a correlation function of the subject non-contact tonometer are adjusted to provide a best fit to the GAT results.

Conducting clinical trials is time consuming and expensive, and therefore clinical calibration might be conducted with respect to a "master" non-contact tonometer, and the master non-contact tonometer is then used as a calibration standard. It is known to measure "IOP" of a set of precision-manufactured rubber eyes designed and tested to applanate at predetermined pressures as a calibration gauge to avoid a clinical trial involving human eyes. Rubber eyes develop folds during testing and tend to be a poor simulation of a real eye. Moreover, rubber eyes are expensive and difficult to manufacture because very tight tolerances are necessary. Finally, the rubber material ages or can be damaged, so that a set of rubber eyes must be constantly recalibrated to maintain reliability.

The Physikalisch-Technische Bundesanstalt (PTB) of Germany developed a calibration tool for non-contact tonometers that employs a mirror and lever system, wherein the tonometer air pulse is directed at a mirror mounted on a lever to angularly displace the lever about a pivot axis. A working version of the tool incorporates a complex assembly of precision moving parts and is available at a cost of close to $30,000.00. Japanese Patent No. 11-225974 describes another mechanical calibration tool generally similar in concept to the PTB calibration tool in that it comprises a mirror mounted for measurable deflection by a tonometer air pulse.

The tonometer calibration devices and methods mentioned above are delicate, expensive, unstable, and/or difficult to use, and they cannot be traced to an absolute pressure standard such as that provided by a water column or precision pressure calibrator.

Against this background, U.S. Pat. No. 6,679,842 issued Jan. 20, 2004 to Luce discloses a tonometer calibration tool mountable in front of an air discharge passage of a non-contact tonometer. The calibration tool includes "an electronic eye" having a pressure sensor for receiving the air pulse and an infra-red emitter connected to the pressure sensor for providing a pseudo-applanation event, such as an infra-red pulse, when the pressure sensor signal reaches a predetermined level. The pulse acts as a pseudo-applanation event because in actual operation, the tonometer detects a peak level of light reflected by a flattened cornea to determine corneal applanation. In this way, the tonometer is induced to measure an applanation event in the absence of an eye. By adjusting the predetermined pressure level to known standards, calibration of the tonometer is possible. The entire disclosure of U.S. Pat. No. 6,679,842 is incorporated herein by reference. The '842 patent and the present invention share common ownership.

While the calibration tool of the '842 patent has greatly simplified calibration procedures, it has the drawback that it is time consuming to set-up. Specifically, the calibration tool of the '842 patent mounts on a fixed external housing of the tonometer, and a movable measurement head of the tonometer must then be aligned in X, Y, and Z dimensions relative to the calibration tool to bring the axis of the fluid discharge passage into alignment with the pressure sensor of the calibration tool and locate an exit end of the discharge passage at a predetermined working distance from the pressure sensor. In this respect, using the calibration tool of the '842 patent is similar to measuring an eye of a patient because the measurement head of the tonometer must first be moved into proper alignment before the air pulse is fired. To carry out this task, the calibration tool of the '842 patent includes a glass sphere 22 by which an opto-electronic alignment system of the tonometer can achieve three-dimensional alignment using light reflected by the glass sphere in the same way the alignment system would align to an eye using light reflected by the cornea. A mirror 26 on the calibration tool may be aligned on test axis in place of glass sphere 22 using a precision slide mechanism to allow for tilt and swivel adjustments. Once these preliminary alignment steps have been completed, the precision slide mechanism is used to insert the pressure sensor on the test axis in place of the mirror, and calibration measurements can be made. The preliminary alignment steps are time consuming, and they require additional parts such as the glass sphere, mirror, and precision slide mechanism that add size and cost to the calibration tool. If proper alignment is not carried out, calibration accuracy may suffer.

What is needed is a tonometer calibration tool that is smaller, less expensive, and easier to use.

SUMMARY OF THE INVENTION

The present invention meets the stated needs and improves upon the calibration tool of U.S. Pat. No. 6,679,842 by reconfiguring the calibration tool to mount directly on a nosepiece of the tonometer or on a measurement head of the tonometer to eliminate alignment steps and parts associate therewith.

In one embodiment, the calibration tool has a mounting orifice for receiving a protruding portion of a tonometer nosepiece, wherein the pressure sensor is arranged to receive an air pulse discharged through a fluid discharge passage of the nosepiece and generate a pressure signal. The orifice may be defined by two body portions adjustably connected to one another to permit the calibration tool to be clamped onto the nosepiece. The calibration tool may include a noise reduction surface between the mounting orifice and the pressure sensor having ridges arranged to affect flow in a zone between an exit end of the tonometer discharge passage and the pressure sensor. The calibration tool includes an emitter triggered when the pressure signal reaches a predetermined level to simulate an applanation event to an applanation detection system of the tonometer.

In another embodiment, the calibration tool has a pair of mounting pins and the measurement head of the tonometer is provided with a corresponding pair of mounting holes for receiving the mounting pins to mount the calibration tool directly on the measurement head of the tonometer.

In accordance with the present invention, the calibration tool is mounted on the tonometer in fixed relation to the fluid discharge passage to eliminate the need for preliminary alignment.

The present invention also encompasses a tonometer calibration method using the improved calibration tool.

BRIEF DESCRIPTION OF THE DRAWING VIEWS

Features and advantages of embodiments of the present disclosure will become apparent by reference to the following detailed description and drawings, in which.

DETAILED DESCRIPTION OF THE INVENTION

The present invention provides a tonometer calibration tool functionally similar to the tonometer calibration tool described in U.S. Pat. No. 6,679,842 already incorporated herein by reference. However, the tonometer calibration tool of the present invention mounts directly on a nosepiece of a non-contact tonometer or on a measurement head of a non-contact tonometer so that it is unnecessary to perform an alignment step during calibration to align the tonometer's test axis with the calibration tool.

Figure 1:
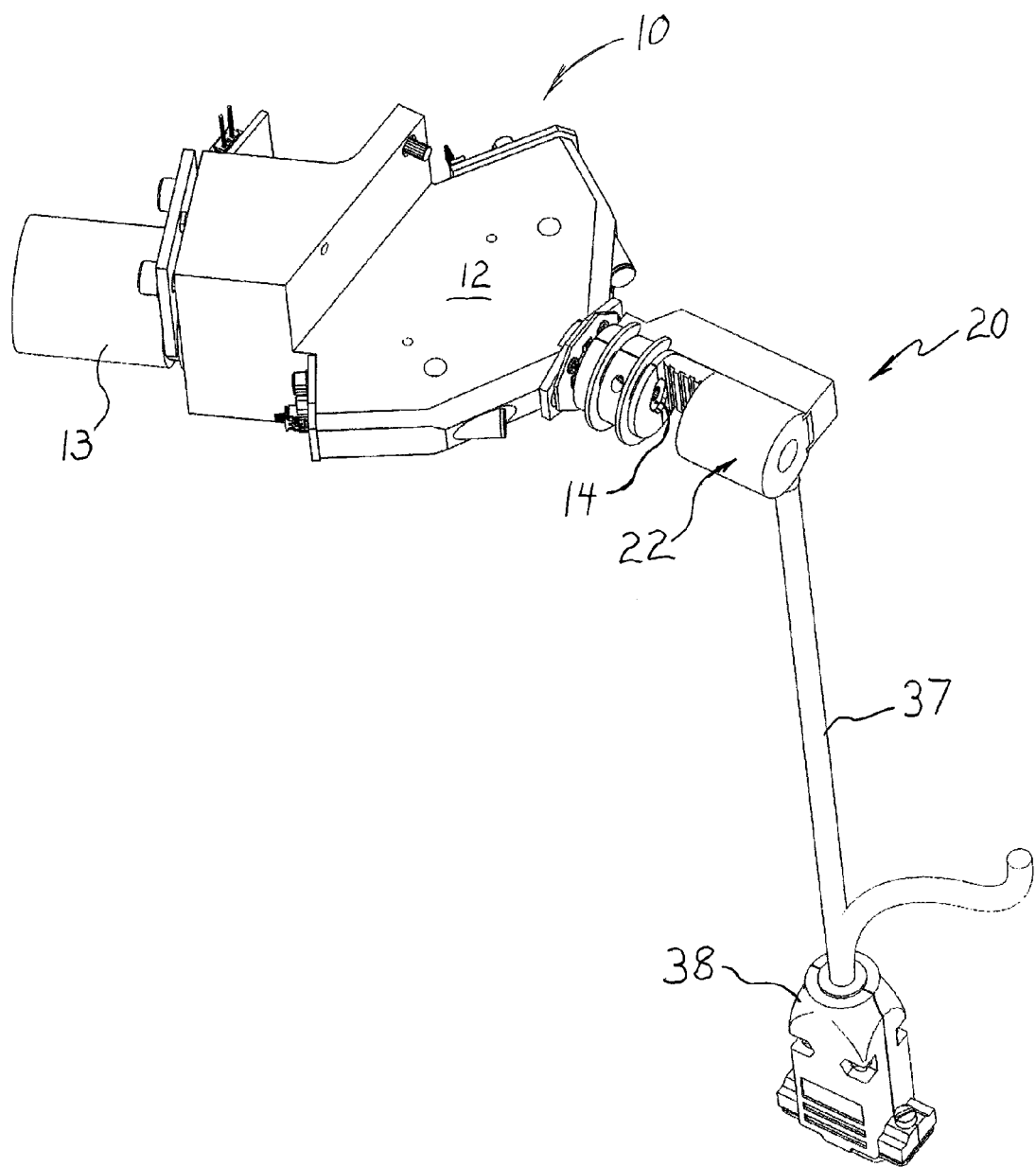
FIG. 1 is a perspective view of a tonometer calibration tool formed in accordance with a first embodiment of the present invention, wherein the tonometer calibration tool is shown mounted on a nosepiece of a non-contact tonometer.
Figure 2:
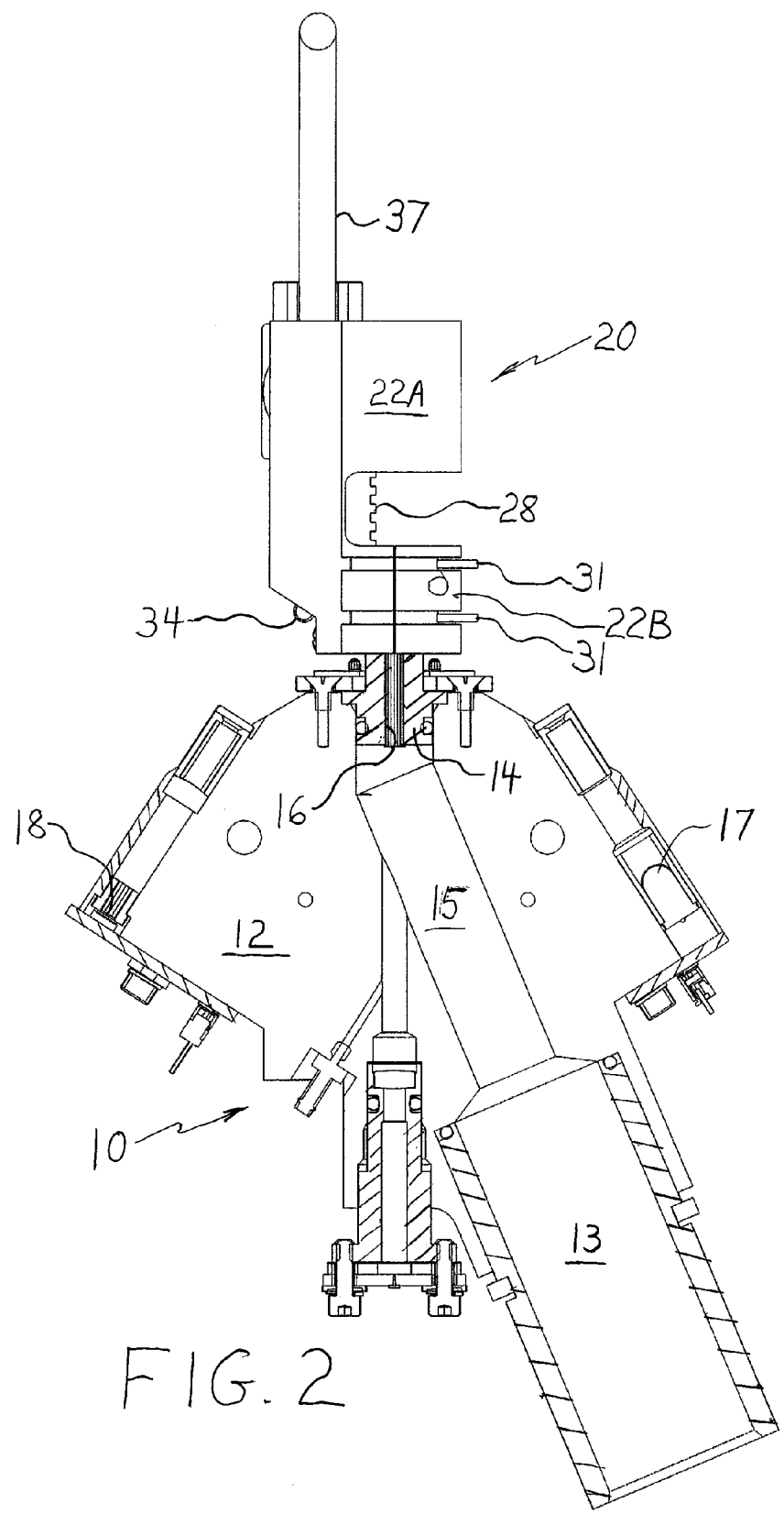
FIG. 2 is a top view of the structure shown in FIG. 1, wherein the nosepiece and a measurement head of the non-contact tonometer are shown sectioned by a horizontal sectioning plane to reveal internal structure thereof.
Figure 3:
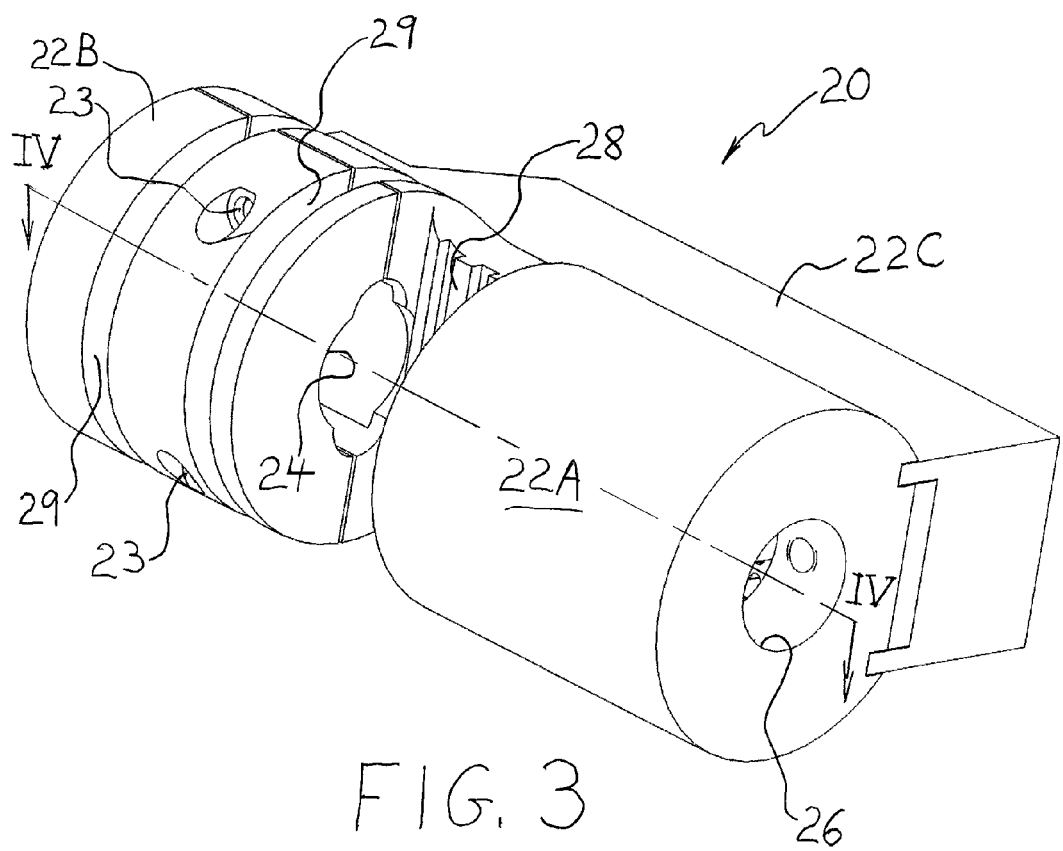
FIG. 3 is an enlarged perspective view of the tonometer calibration tool shown in FIG. 1.

FIGS. 1-4 illustrate a first embodiment of the present invention. In FIG. 1, a non-contact tonometer ("NCT") is identified generally by reference numeral 10. NCT 10 is operable to measure intraocular pressure of an eye by discharging an air pulse at the eye to applanate a cornea of the eye. For this purpose, NCT 10 includes a measurement head 12 and a nosepiece 14 carried by the measurement head, wherein the nosepiece includes a fluid discharge passage 16 for discharging the air pulse along a test axis at the cornea. The air pulse may be generated by a pump mechanism (not shown) communicating with a plenum 13, and the air pulse is conveyed through a conduit 15 in measurement head 12 to discharge passage 16. Discharge passage 16 defines the test axis along which the fluid pulse travels toward the cornea, and may be a passage formed directly within nosepiece 14 or may be formed by a thin tube embedded or fixed in the nosepiece. As will be readily understood by those skilled in the art of non-contact tonometry, measurement head 12 and nosepiece 14 are movable as a unit relative to the cornea to align the test axis with the apex of the cornea for measuring IOP.

Measurement head 12 also includes elements of an opto-electronic applanation detection system for determining the moment when the cornea is applanated by an air pulse so that a corresponding plenum pressure may be determined and correlated with intraocular pressure. More specifically, measurement head 12 includes an infra-red emitter 17 and associated optics for directing a collimated beam obliquely at the cornea, and light-sensitive detector 18 arranged on an opposite side of the test axis for receiving light from the infra-red beam reflected by the cornea. In the absence of corneal deformation cause by the air pulse, the incident collimated beam will become divergent when reflected by the convexly curved surface of the cornea such that the light flux reaching detector 18 will be relatively low. However, when applanation occurs and the surface of the cornea is flat, the incident collimated beam remains substantially collimated after reflection such that light flux reaching detector 18 will be relatively high so as to cause a peak or spike in the detector signal. This type of applanation detection system is already known in the art of non-contact tonometry.

In the first embodiment of the present invention shown in FIGS. 1-4, a tonometer calibration tool 20 is configured to be directly and removably mounted on nosepiece 14. Calibration tool 20 comprises a body 22 having a mating feature in the form of a mounting orifice 24 sized to receive a portion of nosepiece 14. Mounting orifice 24 may be defined by a first body portion 22A and a second body portion 22B adjustable relative to the first body portion 22A along one or more alignment pins 23. In the embodiment shown, first body portion 22A and second body portion 22B have opposing concave recesses for defining mounting orifice 24. Body 22 may have one or more annular slots 29 around the second body portion 22B and the opposing region of first body portion 22A for receiving C-clips 31 in spring-loaded fashion, whereby body 22 may be clamped onto a portion of nosepiece 14 projecting from measurement head 12. Of course, numerous alternative means are available to urge body portions 22A and 22B together, for example screws, magnets, o-rings, and other spring configurations.

Alternatively, body 22 may be a unitary structure including a non-adjustable mounting orifice having an inner diameter substantially matched to an outer diameter of nosepiece 14 to allow body 22 to slidably receive the protruding portion of nosepiece 14 in close fit.

Calibration tool 20 also comprises a pressure sensor 30 carried by body 22 and arranged to receive the air pulse when body 22 is mounted on nosepiece 14. Pressure sensor 30 provides a pressure signal in response to the air pulse. Pressure sensor 30 may be arranged in a cavity 26 within first body portion 22A in axial alignment with mounting orifice 24. Pressure sensor may be located at a reference distance from an end of body 22 that abuts against measurement head 12 such that the pressure sensor will be positioned at a predetermined working distance from an exit end of discharge passage 16 when calibration tool 20 is mounted on nosepiece 14.

Body 22 may include a noise reduction surface 28 separating pressure sensor 30 from mounting orifice 24. Noise reduction surface 28 has a plurality of ridges 28A separated by troughs 28B. Ridges 28A extend in a direction non-parallel to the test axis and the axial direction of mounting orifice 24. In the embodiment depicted in FIGS. 1-4, the ridges of noise reduction surface 28 are arranged to extend in a direction orthogonal to the test axis and the axial direction of mounting orifice 24. As seen in FIGS. 1-4, body 22 may be open across noise reduction surface 28. It has been found through empirical observation that providing noise reduction surface 28 substantially reduces signal noise in the pressure signal generated by pressure sensor 30.

Calibration tool 20 further comprises a radiation emitter 34 carried by body 22. Radiation emitter 34 provides a pseudo-applanation event when the pressure signal from pressure sensor 30 reaches a predetermined level. The pseudo-applanation event may be in the form of a brief pulse of light, for example infra-red light, to mimic reflection of an obliquely incident collimated beam from the cornea as described above. Thus, the pseudo-applanation event is detectable by NCT 10 as though an actual corneal applanation had taken place. Emitter 34 is chosen to emit radiation detectable by detector 18 of NCT 10. Consequently, the type of emitter used will depend on the type of applanation detection system employed by NCT 10.

Figure 4:
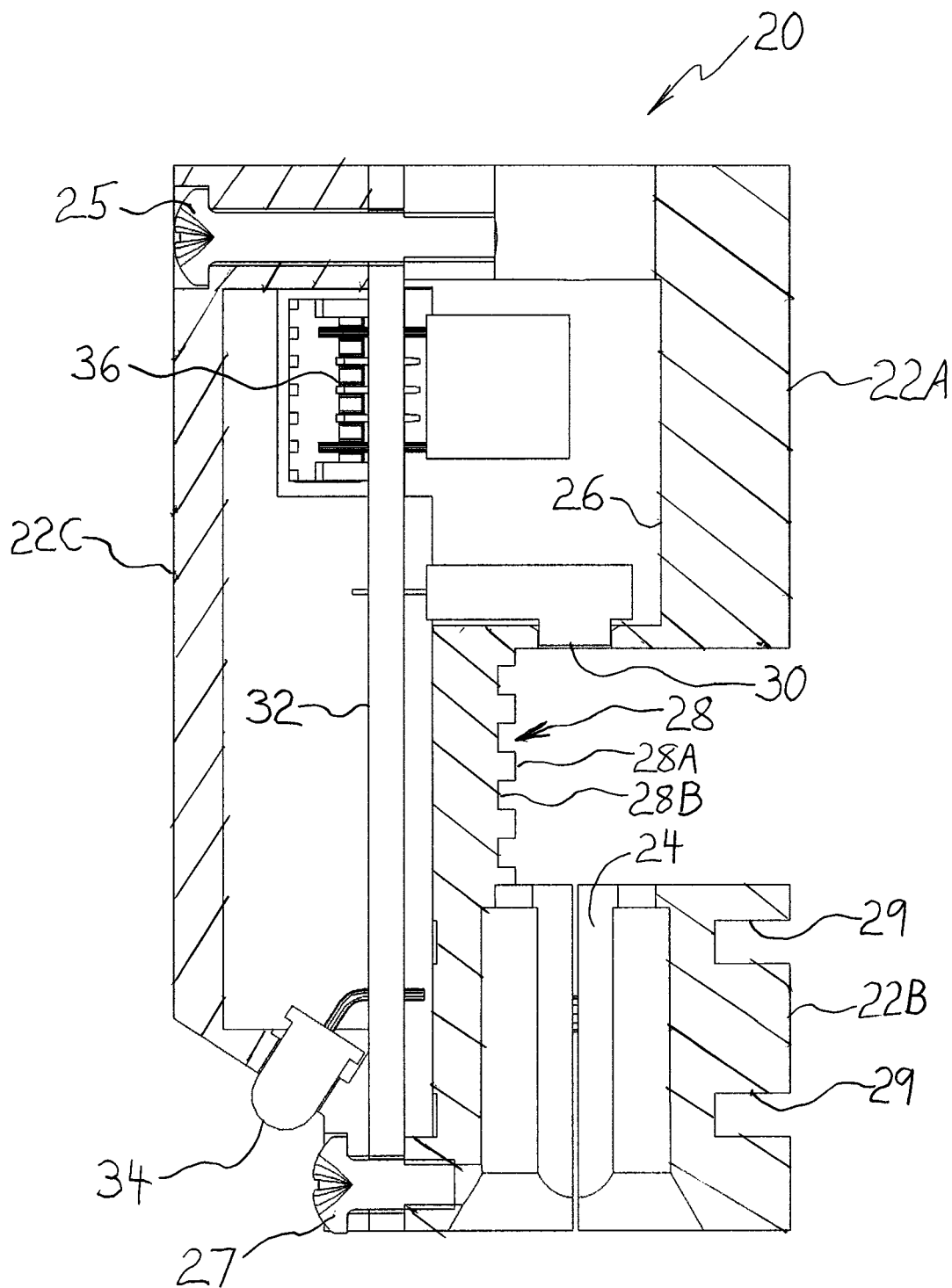
FIG. 4 is an enlarged sectional view of the tonometer calibration tool taken generally along the line IV-IV in FIG. 3.

As best seen in FIG. 4, pressure sensor 30 and emitter 34 are connected to a printed circuit board 32 having a data input/output connection 36 for connecting printed circuit board to an external controller (not shown) as described in U.S. Pat. No. 6,679,842 referenced above. Connection may be made by way of cable 37 and connector 38 depicted in FIG. 1. Wireless communication with a controller is also contemplated. Printed circuit board 32 and emitter 34 may be mounted on a third body portion 22C removably coupled to first body portion 22A by threaded fasteners 25 and 27.

FIGS. 5-8 show a tonometer calibration tool 40 formed in accordance with a second embodiment of the present invention. Calibration tool 40 comprises a body 42 configured to be directly and removably mounted on measurement head 12 of NCT 10 instead of nosepiece 14. More specifically, body 42 includes a mating feature in the form of a pair of mounting pins 44A, 44B sized for receipt by a corresponding pair of mounting holes 19A, 19B in measurement head 12. One of the mounting pins may be hexagonal (see mounting pin 44B in FIG. 7) to facilitate insertion of mounting pins 44A, 44B into mounting holes 19A, 19B.

Body 42 includes a sensor portion 41 for housing pressure sensor 30 and emitter 34. In the embodiment shown, sensor portion 41 includes a sensor block 42A and a support member 42D. Body 42 also includes a mounting block 42B from which the pair of mounting pins 44A, 44B extend and a bridge member 42C connecting sensor portion 41 to mounting block 42B. Sensor block 42A may be fixed to bridge member 42C by way of support member 42D. Body 42 is configured such that pressure sensor 30 is arranged on the test axis to receive the air pulse when body 42 is mounted on measurement head 12 of NCT 10.

Figure 5:
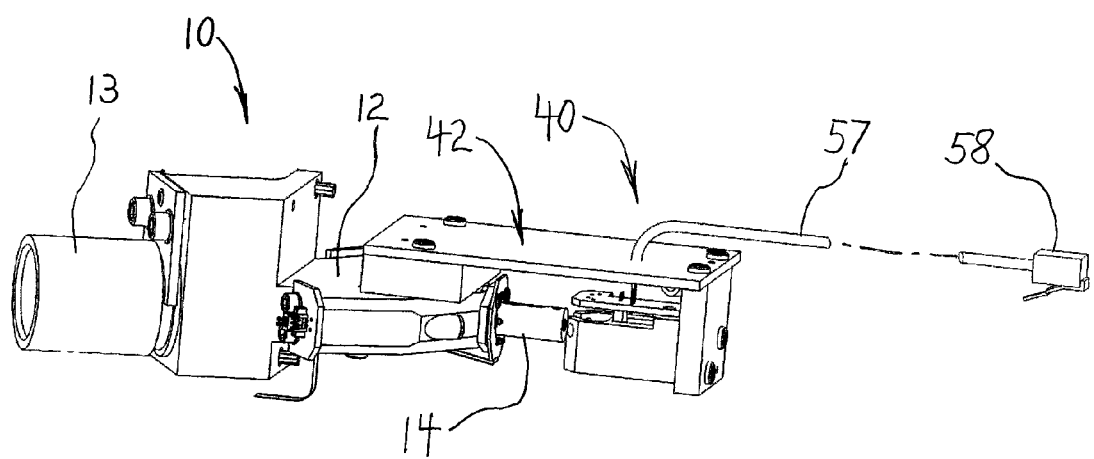
FIG. 5 is a perspective view of a tonometer calibration tool formed in accordance with a second embodiment of the present invention, wherein the tonometer calibration tool is shown mounted on a measurement head of a non-contact tonometer.
Figure 6:
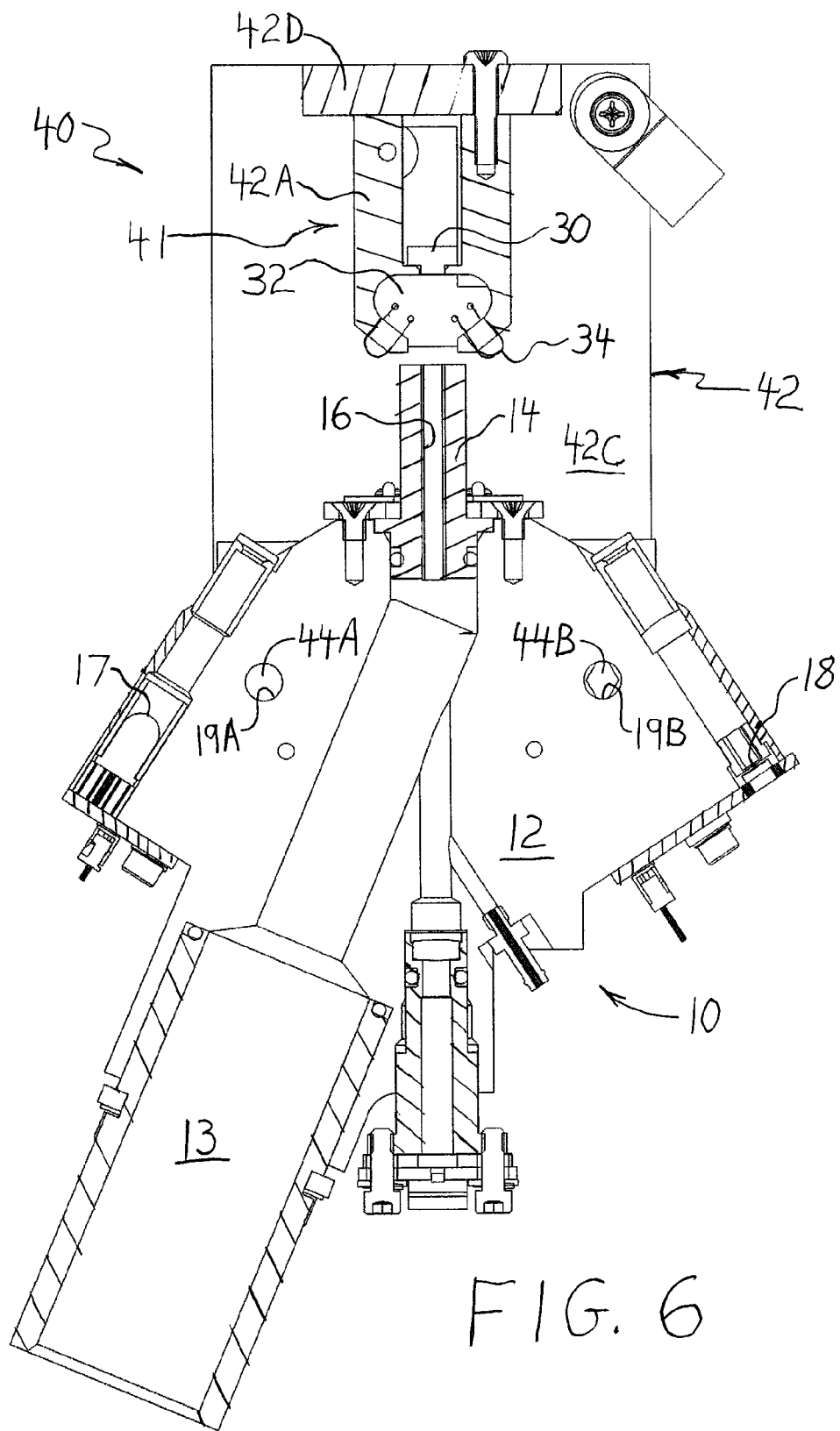
FIG. 6 is a bottom view of the structure shown in FIG. 5, wherein the measurement head and a nosepiece of the non-contact tonometer, and the calibration tool, are shown sectioned by a horizontal sectioning plane to reveal internal structure thereof.
Figure 7:
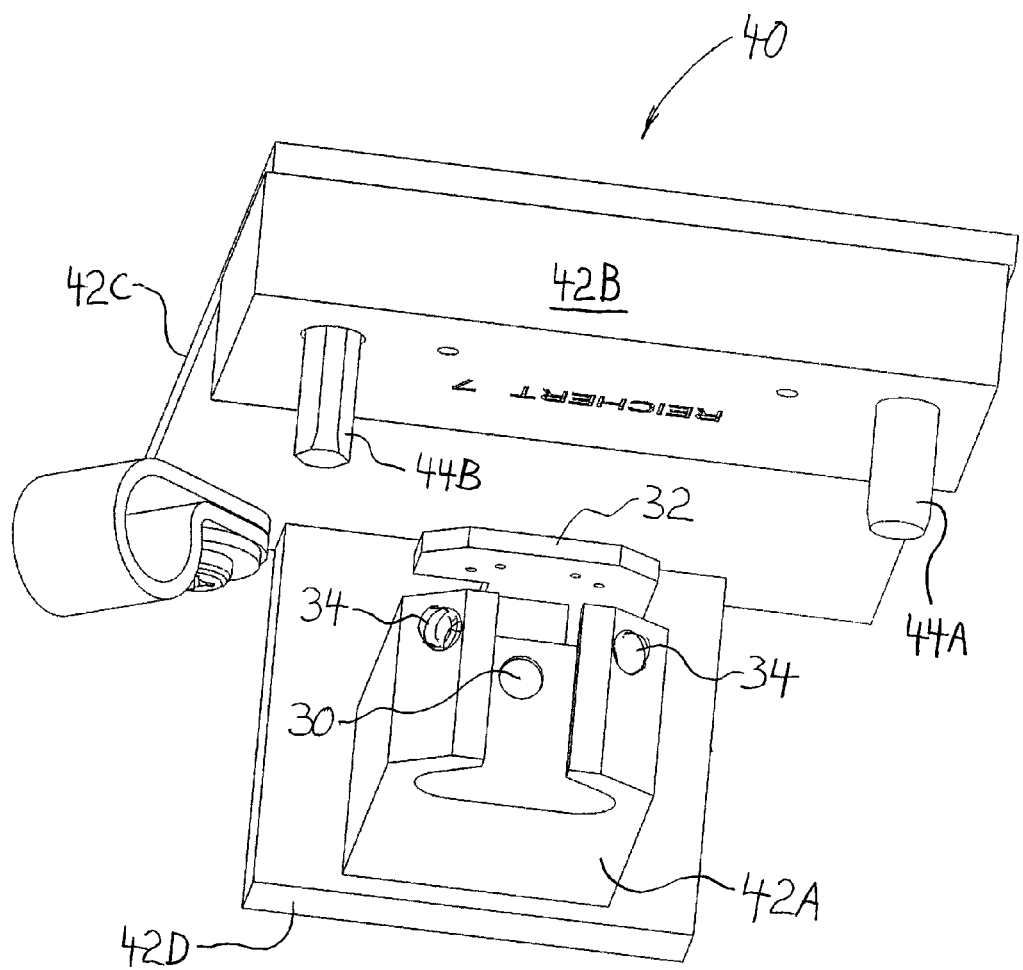
FIG. 7 is an enlarged perspective view of the tonometer calibration tool shown in FIG. 5.
Figure 8:
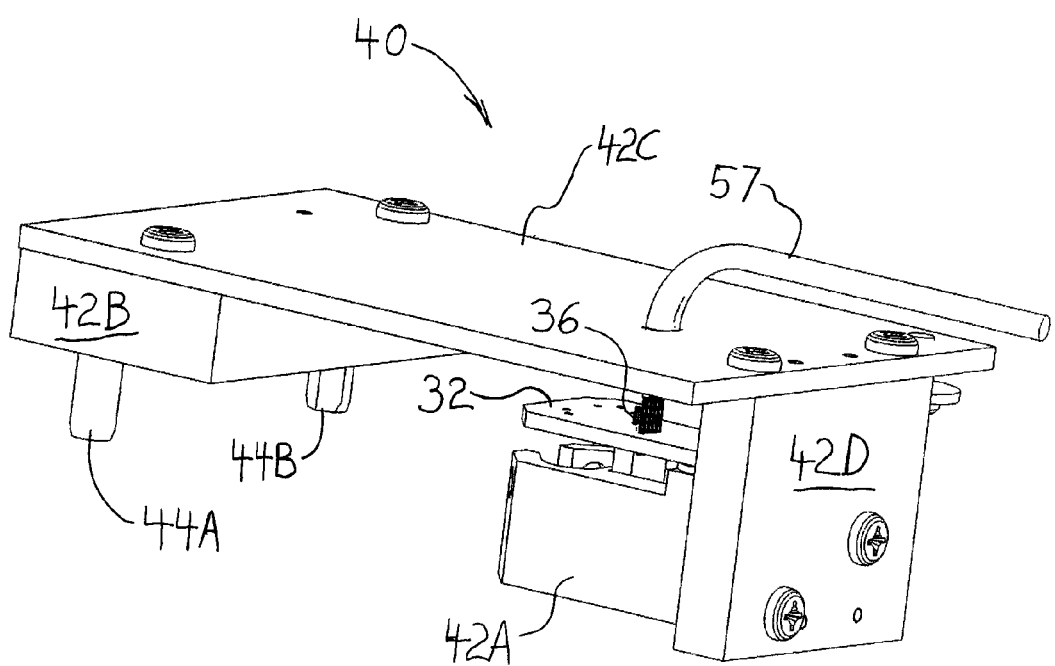
FIG. 8 is another perspective view of the tonometer calibration tool shown in FIG. 5.

Like the calibration tool 20 of the first embodiment, calibration tool 40 of the second embodiment carries the printed circuit board 32 and its associated data input/output connection 36. As shown in FIG. 5, a cable 57 and connector 58 may be provided for connection to a controller (not shown).

As will be understood, the present invention provides a more user-friendly method of calibrating a non-contact tonometer that eliminates time-consuming alignment steps. In accordance with the calibration tool embodiments described above, the method comprises the steps of (A) mounting a tonometer calibration tool 20, 40 on the nosepiece 14 or the measurement head 12 of NCT 10 such that the pressure sensor 30 is arranged to receive the air pulse; (B) operating NCT 10 to direct an air pulse onto pressure sensor 30; (C) comparing a pressure signal from pressure sensor 30 with a predetermined signal level corresponding to a known IOP measurement standard; (D) inducing NCT 10 to detect applanation when the pressure signal from pressure sensor 30 reaches the predetermined signal level such that the NCT provides a measured pressure value; and (E) adjusting at least one parameter of a correlation function of the NCT to reduce a difference between the measured pressure value and the known IOP measurement standard. The method may comprise further steps of adjusting the predetermined signal level to a different value and repeating steps (B) through (E) above.

While the invention has been described in connection with exemplary embodiments, the detailed description is not intended to limit the scope of the invention to the particular forms set forth. The invention is intended to cover such alternatives, modifications and equivalents of the described embodiment as may be included within the spirit and scope of the invention.

LIST OF REFERENCE SIGNS

10 Non-contact tonometer (NCT)
12 Measurement head
13 Plenum
14 Nosepiece
15 Conduit
16 Fluid discharge passage
17 Emitter
18 Detector
19A, 19B Mounting holes
20 Tonometer calibration tool (first embodiment)
22 Body of calibration tool 20
22A First body portion of body 22
22B Second body portion of body 22
22B Third body portion of body 22
23 Alignment pins
24 Mounting orifice
26 Cavity
28 Noise reduction surface
28A Ridges of noise reduction surface
28B Troughs of noise reduction surface
30 Pressure sensor
32 Printed circuit board
34 Emitter
36 Connection port
37 Cable
38 Connector
40 Tonometer calibration tool (second embodiment)
41 Sensor portion
42 Body of calibration tool 4
42A Sensor block of body 42
42B Mounting block of body 42
42C Bridge member of body 42

42D Support member of body 42
44A, 44B Mounting pins
57 Cable
58 Connector

What is claimed is:

1. A calibration system comprising, in combination:
a non-contact tonometer operable to measure intraocular pressure of an eye by discharging an air pulse at the eye to applanate a cornea of the eye, the non-contact tonometer including a nosepiece including a fluid discharge passage for discharging the air pulse along a test axis at the cornea, wherein the nosepiece is movable relative to the cornea to align the test axis with the cornea; and
a tonometer calibration tool removably mounted on the nosepiece, the calibration tool including (i) a pressure sensor arranged to receive the air pulse to provide a pressure signal in response to the air pulse and (ii) a radiation emitter, wherein the radiation emitter provides a pseudo-applanation event when the pressure signal reaches a predetermined level, the pseudo-applanation event being detectable by the non-contact tonometer as though an actual corneal applanation had taken place;
wherein the tonometer calibration tool further includes a mounting orifice receiving a portion of the nosepiece to removably mount the tonometer calibration tool on the nosepiece.

2. The calibration system according to claim 1, wherein the pressure sensor is arranged in alignment with test axis.

3. The calibration system according to claim 2, wherein the calibration tool includes a noise reduction surface separating the pressure sensor from the mounting orifice, the noise reduction surface having a plurality of ridges extending in a direction non-parallel to the test axis.

4. The calibration system according to claim 3, wherein the calibration tool is open across the noise reduction surface.

* * * * *